(12) United States Patent
Ku et al.

(10) Patent No.: US 9,575,041 B2
(45) Date of Patent: Feb. 21, 2017

(54) GAS CROSS-SENSITIVITY ANALYSIS METHOD AND SYSTEM THEREOF

(71) Applicant: Automotive Research & Testing Center, Changhua County (TW)

(72) Inventors: Yong-Yuan Ku, Changhua County (TW); Ya-Lun Chen, Changhua County (TW); Chia-Jui Chiang, Changhua County (TW); Yu-Hsuan Su, Changhua County (TW); Chih-Cheng Chou, Changhua County (TW)

(73) Assignee: Automotive Research & Testing Center, Changhua County (TW)

( * ) Notice: Subject to any disclaimer, the term of this patent is extended or adjusted under 35 U.S.C. 154(b) by 311 days.

(21) Appl. No.: 14/334,760

(22) Filed: Jul. 18, 2014

(65) Prior Publication Data
US 2015/0276698 A1 Oct. 1, 2015

(30) Foreign Application Priority Data
Mar. 26, 2014 (TW) .............................. 103111284 A

(51) Int. Cl.
*G01N 33/00* (2006.01)
*F01N 3/20* (2006.01)

(52) U.S. Cl.
CPC ......... *G01N 33/0037* (2013.01); *F01N 3/2066* (2013.01); *G01N 33/0054* (2013.01)

(58) Field of Classification Search
CPC ............. F01N 2560/026; F01N 3/2066; G01N 27/407; G01N 33/0037; G01N 33/0054
USPC ........................................... 73/23.31, 114.73
See application file for complete search history.

(56) References Cited

U.S. PATENT DOCUMENTS

| | | | |
|---|---|---|---|
| 7,854,161 B2 | 12/2010 | Hjorsberg et al. | |
| 8,061,126 B2 * | 11/2011 | Gady .................... | B01D 53/30 60/286 |
| 8,096,110 B2 | 1/2012 | Solbrig | |
| 8,281,578 B2 | 10/2012 | Upadhyay et al. | |
| 8,453,434 B2 | 6/2013 | Yacoub | |
| 8,510,024 B2 | 8/2013 | Gady et al. | |
| 8,635,007 B2 | 1/2014 | Balenovic et al. | |

(Continued)

FOREIGN PATENT DOCUMENTS

CN 102854184 A 1/2013

OTHER PUBLICATIONS

Chih-Cheng Chou et al., Interpretation of the Oscillating Signals of the Smart NOx Sensors used in Urea Selective Catalyst Reduction Systems via Spectral Analysis, Applied Mechanics and Materials, vols. 479-480, Published on Dec. 2013.

*Primary Examiner* — Freddie Kirkland, III
(74) *Attorney, Agent, or Firm* — CKC & Partners Co., Ltd.

(57) ABSTRACT

A gas cross-sensitivity analysis method is provided. The method includes, an injection frequency signal is generated from a first gas. A second gas sensing signal is captured from a second gas. Then, the second gas sensing signal is converted to a second gas sensing frequency signal by using Fast Fourier Transform. Further, a sensing peak frequency signal is determined from peak frequency of the second gas sensing frequency signal. The injection frequency signal and the sensing peak frequency signal are analyzed. A gas cross-sensitivity effect can be direct interpretation by a singular indication between the injection frequency signal and the sensing peak frequency signal.

9 Claims, 5 Drawing Sheets

(56) References Cited

U.S. PATENT DOCUMENTS

| | | | |
|---|---|---|---|
| 8,881,508 B2* | 11/2014 | Geveci | G01N 27/407 60/276 |
| 2010/0170226 A1 | 7/2010 | Prakash et al. | |
| 2011/0005209 A1 | 1/2011 | Gady et al. | |
| 2011/0185707 A1 | 8/2011 | Upadhyay et al. | |
| 2011/0262329 A1 | 10/2011 | Ofoli et al. | |
| 2012/0017568 A1 | 1/2012 | Geveci et al. | |
| 2012/0023907 A1 | 2/2012 | Brahma et al. | |
| 2012/0144801 A1 | 6/2012 | Levijoki et al. | |
| 2012/0233986 A1 | 9/2012 | Geveci et al. | |
| 2012/0310507 A1 | 12/2012 | Auckenthaler | |
| 2013/0000278 A1 | 1/2013 | Dubkov et al. | |
| 2014/0202233 A1* | 7/2014 | Itaya | G01N 33/007 73/23.31 |

* cited by examiner

GAS CROSS-SENSITIVITY ANALYSIS METHOD AND SYSTEM THEREOF

RELATED APPLICATIONS

This application claims priority to Taiwan Application Serial Number 103111284, filed Mar. 26, 2014, which is herein incorporated by reference.

BACKGROUND

Technical Field

The present disclosure relates to a sensing signal analysis method and a system thereof. More particularly, the present disclosure relates to a gas cross-sensitivity effect analysis method and a system thereof.

Description of Related Art

Acid rains, depletion of ozone and photochemical smog, produced by $NO_X$, $SO_X$, and other volatile organic compounds, have constituted enormous threat to human health and ecological environment. The emission of $SO_X$ and other volatile organic compounds have been substantially reduced by the improved oil refinery techniques. Therefore, the removal of $NO_X$ from waste gases has already become one of the most important tasks of environmental pollution treatment in the 21st century.

Using urea solution as a reductant, selective catalyst reduction (SCR) is one of the most effective aftertreatment systems for reducing engine exhaust NOx emission. The NGK/Continental Smart NOx Sensor (SNS) is widely used for exhaust aftertreatment systems such as SCR. The output signal of the SNS, however, is characterized with different levels of oscillation as the urea injection changes. Moreover, due to the cross-sensitivity of the SNS to the ammonia concentration for higher-than-stoichiometric ammonia injection, the sensor signal cannot be interpreted in a straight-forward way as it is not clear whether excess $NO_X$ or $NH_3$ is present. So that it not only causing the logic errors of the SCR aftertreatment systems and the excess ammonia injection causing wasteful, but also the contaminants produced by excess ammonia and $SO_X$ causing reduced the efficiency of the SCR aftertreatment systems.

Prior arts attempt to solve this problem of gas cross-sensitivity of the SCR aftertreatment systems. As is known, one is placed two SNS on upstream and downstream of the SCR aftertreatment systems to determine the ammonia concentration excess or not. Another is installed a chemiluminescence analyzer to calculate the ammonia concentration. As mention above, prior arts need to install another SNS or apparatus, increase not only cost but also system weight and complication.

SUMMARY

According to one aspect of the present disclosure, a gas cross-sensitivity analysis method is provided. The method includes, an injection frequency signal is generated from a first gas. A second gas sensing signal is captured from a second gas. Then, the second gas sensing signal is converted to a second gas sensing frequency signal. Further, a sensing peak frequency signal is determined from peak frequency of the second gas sensing frequency signal. The injection frequency signal and the sensing peak frequency signal are analyzed wherein a gas cross sensitivity effect is occurred due to a singular indication between the injection frequency signal and the sensing peak frequency signal.

According to another aspect of the present disclosure, a gas cross-sensitivity analysis system is provided. The system includes a first gas generating unit, a second sensing unit, a signal converting unit, a peak frequency judging unit and a signal analyzing unit. The first gas generating unit is generated an injection frequency signal from a first gas. The second sensing unit is captured a second gas sensing signal from a second gas. The signal converting unit is electrically connected to the second sensing unit, and converted the second gas sensing signal to a second gas sensing frequency signal using a Fast Fourier Transform. The peak frequency judging unit is electrically connected to the signal converting unit, and determined a peak frequency of the second gas sensing frequency signal and outputted a sensing peak frequency signal. The signal analyzing unit is electrically connected to the first gas generating unit and the peak frequency judging fruit, and analyzed the injection frequency signal and the sensing peak frequency signal.

BRIEF DESCRIPTION OF THE DRAWINGS

The present disclosure can be more fully understood by reading the following detailed description, with reference made to the accompanying drawings as follows.

DETAILED DESCRIPTION

Figure 1:
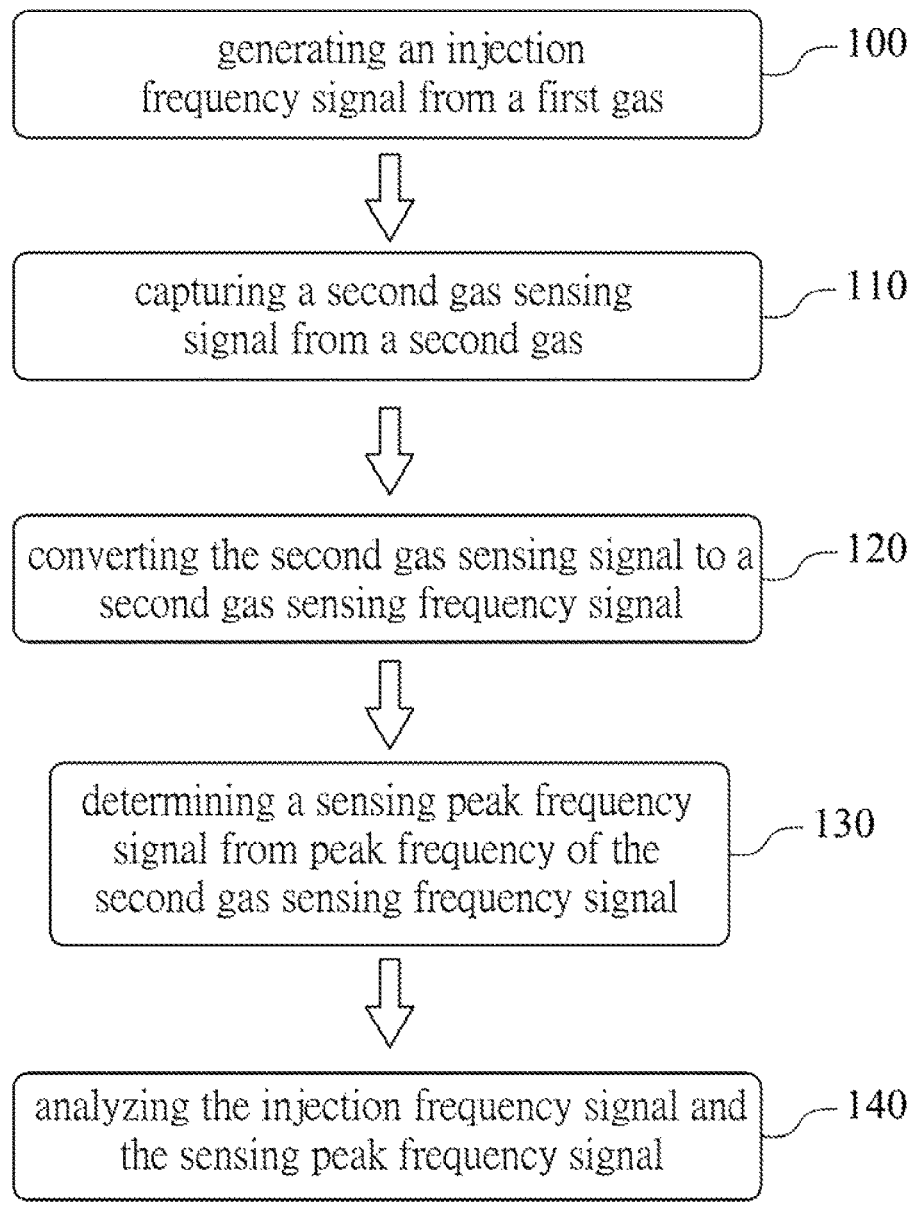
FIG. 1 is a flowchart of a gas cross-sensitivity analysis method according to one embodiment of the present disclosure.

FIG. 1 is a flowchart of a gas cross-sensitivity analysis method according to one embodiment of the present disclosure, and the method includes the following steps. Step 100, generating an injection frequency signal from a first gas. Step 110, capturing a second gas sensing signal from a second gas. Step 120, converting the second gas sensing signal to a second gas sensing frequency signal. Step 130, determining a sensing peak frequency signal from peak frequency of the second gas sensing frequency signal. Step 140, analyzing the injection frequency signal and the sensing peak frequency signal. When the injection frequency signal and the sensing peak frequency signal are singular referring to a gas cross-sensitivity effect is occurred.

As mentioned of the second gas sensing signal is converted to the second gas sensing frequency signal using a Fast Fourier Transform (FFT). FFT computes Discrete Fourier Transform (DFT) in an efficient manner. In OFT, the sequence of N data points x(0), x(1), . . . , x(N−1) is transformed into the list of coefficients of a finite combination of complex sinusoids, ordered by their frequencies. The equation is stated as following.

$$X(k) = \sum_{n=0}^{N-1} x(n) e^{-j(\frac{2\pi}{N})kn}$$

Further, in step 140, the injection frequency signal ($f_{pump}$) and the sensing peak frequency signal ($f_{peak}$) are analyzed, that is, a subtracted value ($f_{peak}-f_{pump}$) is provided by subtracting the sensing peak frequency signal from the injection frequency signal, and a difference ($|f_{peak}-f_{pump}|$) is provided by taking an absolute value of the subtracted value. Then the difference is compared to a standard value ($\epsilon$). If the difference is less than the standard value ($|f_{peak}-f_{pump}|<\epsilon$) indicating the second gas sensing signal being correct, otherwise the difference is greater than the standard value ($|f_{peak}-f_{pump}|>\epsilon$) indicating the second gas sensing signal being error.

In detail, the sensing peak frequency signal can include the first peak frequency signal ($f_{peak}^{1st}$) and the second peak frequency signal ($f_{peak}^{2nd}$). The first peak frequency signal is the highest peak of second gas sensing frequency signal, and the second peak frequency signal is the sub-highest peak of second gas sensing frequency signal. The injection frequency signal is subtracted to the first peak frequency signal, and taken absolute value, and produced a first difference ($|f_{peak}^{1st}-f_{pump}|$); the injection frequency signal is subtracted to the second peak frequency signal, and taken absolute value, and produced a second difference ($|f_{peak}^{2nd}-f_{pump}|$). Then the first difference and the second difference are compared to the standard value ($\epsilon$). If the first difference and the second difference are both less than the standard value indicating the second gas sensing signal being correct. Otherwise, if at least one of the first difference and the second difference is greater than the standard value indicating the second gas sensing signal being error and referring to occurred gas cross-sensitivity effect. The second peak frequency sign ($f_{peak}^{2nd}$) is an authentication for avoiding the influence of the algorithm interpretation.

When the error is determined, the leakage of urea is occurred. The leakage urea concentration is related to the first peak frequency signal ($f_{peak}^{1st}$). Let the first peak frequency signal multiplied by a gain ($\sigma$) from experiment to estimate the leakage urea concentration. It can be express by $(NH_3)_{leakage}=\sigma \cdot (\max X(K))$.

The standard value is set for avoiding the error caused by lacked frequency resolution between the peak frequency signal and the injection frequency signal. The standard value is determined by the sampling time of FFT, wherein the standard value is negatively correlated to the sampling time. That is, the standard value can be designed smaller according to the longer sampling time, or can be designed greater according to the shorter sampling time.

Figure 2:
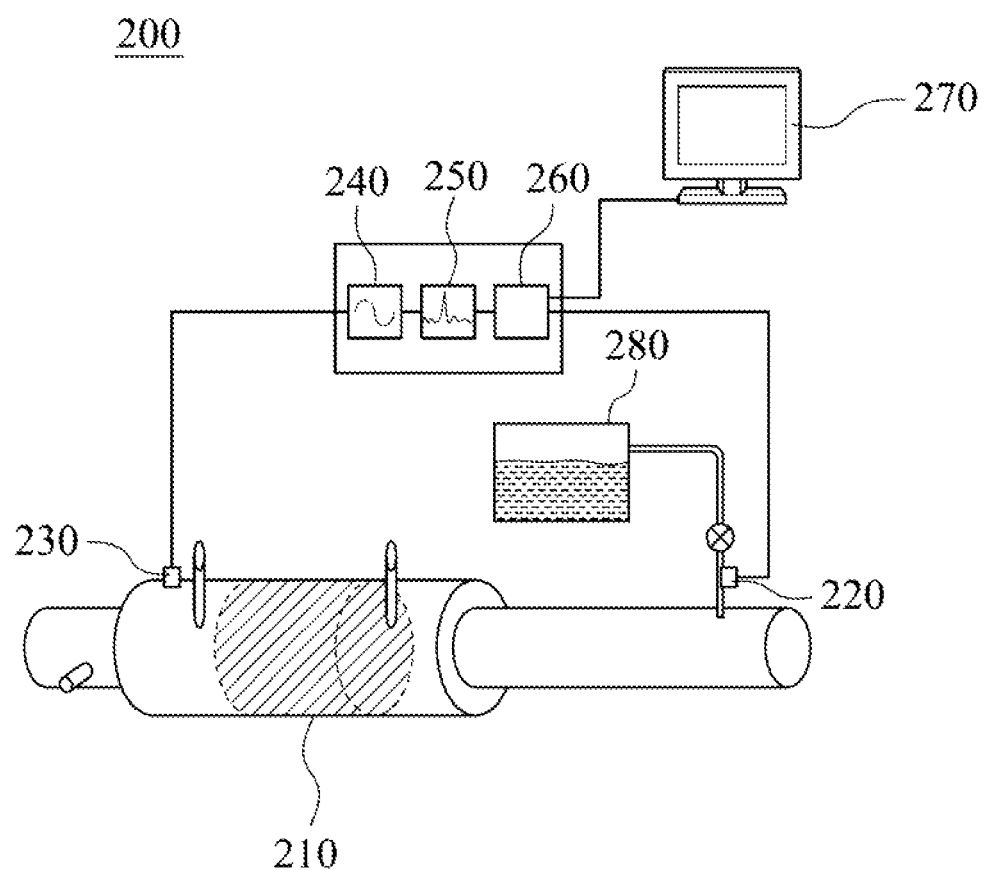
FIG. 2 is a schematic diagram of a gas cross-sensitivity analysis system according to another embodiment of the present disclosure.

FIG. 2 is a schematic diagram of a gas cross-sensitivity analysis system 200 according to another embodiment of the present disclosure. The gas cross-sensitivity analysis system 200 includes a first gas generating unit 220, a second sensing unit 230, a signal converting unit 240, a peak frequency judging unit 250 and a signal analyzing unit 260. The first gas generating unit 220 is generated an injection frequency signal from a first gas. The second sensing unit 230 is captured a second gas sensing signal from a second gas. The signal converting unit 240 is electrically connected to the second sensing unit 230, and converted the second gas sensing signal to a second gas sensing frequency signal using a Fast Fourier Transform. The peak frequency judging unit 250 is electrically connected to the signal converting unit 240, and determined a peak frequency of the second gas sensing frequency signal and outputted a sensing peak frequency signal. The signal analyzing unit 260 is electrically connected to the first gas generating unit 220 and the peak frequency judging unit 250, and analyzed the injection frequency signal and the sensing peak frequency signal.

Moreover, the gas cross-sensitivity analysis system 200 in FIG. 2 can further include a selective catalytic reduction unit (hereafter SCR) 210. The SCR 210 is used to convert the second gas into a non-toxic gas by using the first gas.

As mentioned of the gas cross-sensitivity analysis system 200, wherein the signal analyzing unit 260 is electrically connected to a display unit 270. The display unit 270 not only displays the injection frequency signal and the sensing peak frequency signal, but also displays the result of the gas cross-sensitivity effect which determined by the signal analyzing unit 260.

In the embodiment of FIG. 2, the first gas is ammonia, and the second gas is nitrogen oxide. The gas cross-sensitivity analysis system 200 can further include a urea (($NH_2)_2CO$) tank 280 for containing urea aqueous solution. The $NH_3$ (the first gas) is produced from vaporization of urea aqueous solution, and supplied for SCR 210. The chemical reaction of urea evaporating into $NH_3$ is presented as follow:

$$(NH_2)_2CO+H_2O \rightarrow 2NH_3CO_2$$

The SCR reduces the engine-out $NO_X$ emission mainly via a series of reactions including evaporation of the urea aqueous solution, decomposition of the urea molecules, $NH_3$ adsorption and desorption on the catalyst surface, and reduction of $NO_X$. The chemical reaction as mentioned above is presented as follow:

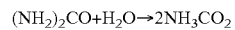
$$6NO+4NH_3 \leftrightarrow 5N_2+6H_2O;$$

$$4NO+4NH_3+O_2 \leftrightarrow 4N_2+6H_2O;$$

$$6NO_2+8NH_3 \leftrightarrow 7N_2+12H_2O;$$

$$2NO_2+4NH_3+O_2 \leftrightarrow 3N_2+6H_2O; \text{ and}$$

$$NO+NO_2+2NH_3 \leftrightarrow 2N_2+3H_2O.$$

As mentioned of the SCR 210, wherein a catalyst material can use $V_2O_5$. $WO_3$ or $TiO_2$.

As mentioned of the second sensing unit 230 can be a Smart $NO_X$ sensor (hereafter "SNS"). The SNS consists mainly of three parts, including the sensor body, control module and transmission harness. The sensor body is manufactured using the material of zirconia ($ZrO_2$) with an integrated heater, two cavities and three oxygen pumps. The heater is integrated in the sensor body to raise the temperature up to 800° C. Due to the cross-sensitivity of the SNS to the ammonia concentration for higher-than-stoichiometric ammonia injection, the second gas sensing signal cannot be interpreted in a straight-forward way as it is not clear whether $NO_X$ or $NH_3$ is excess. In the present disclosure, the second gas sensing signal observed by the SNS is explained by conducting spectral analysis using FFT. Different oscillating behaviors are illustrated via the nonlinearly between the $NH_3$ injection and the $NO_X$ concentration downstream SCR. The amplitude of the second gas sensing signal at a perturbed injection frequency can be used for direct interpretation of the true $NO_X$ emission in systems when ammonia is involved.

Figure 3A:
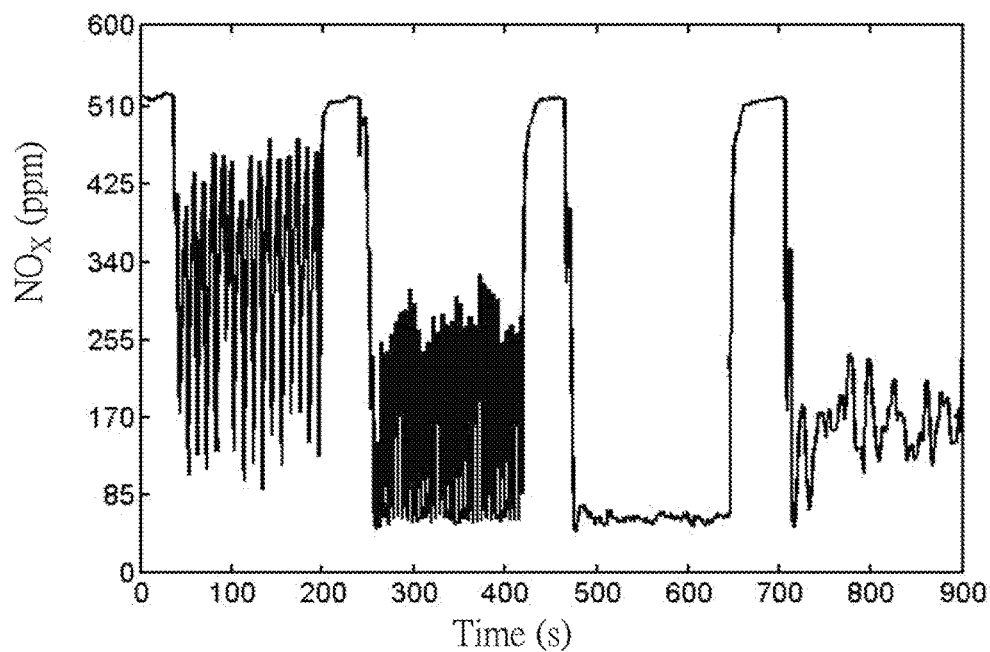
FIG. 3A illustrates a NOx concentration (ppm)—Time diagram measuring from the second sensing unit of FIG. 2.
Figure 3B:
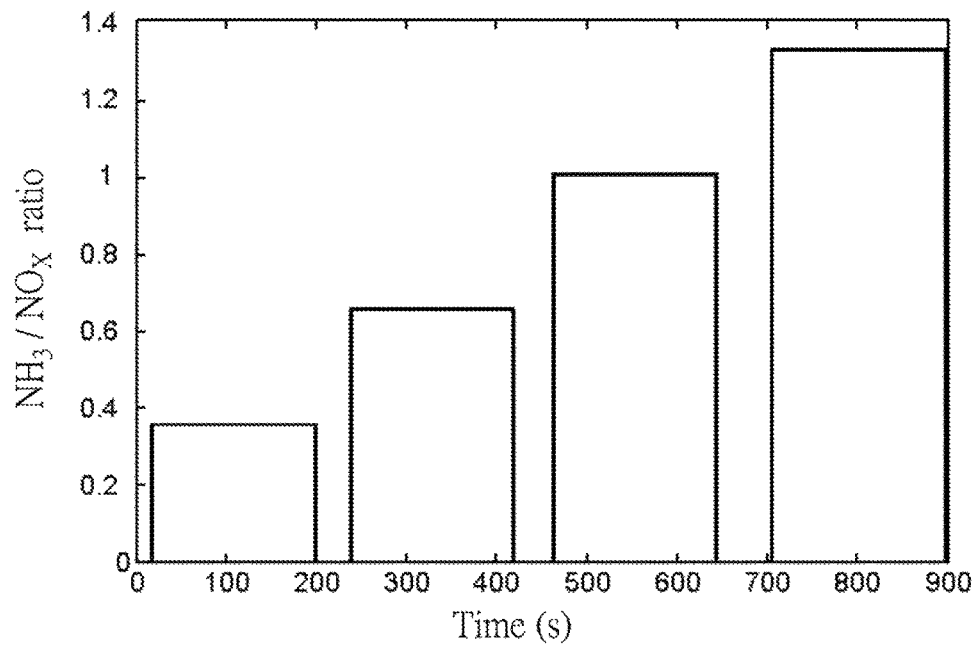
FIG. 3B illustrates a concentration ratio between $NH_3$ and $NO_X$ ($NH_3/NO_X$)—Time(s) diagram of FIG. 3A.

FIG. 3A illustrates a $NO_X$ concentration (ppm)–Time(s) diagram measuring from the second sensing unit 230 of FIG. 2. FIG. 3B illustrates a concentration ratio between $NH_3$, and $NO_X$ ($NH_3/NO_X$)–Time(s) diagram of FIG. 3A.

In FIG. 3B, the measuring time of SNS is about 900 sec; the concentration ratio $NH_3/NO_X$ is step-increased four times by urea pumping speed, wherein the ratio is about 0.35, 0.65, 1 and 1.35. By increasing the $NH_3$ injection frequency for increasing the amount of $NH_3$, and enhancing the ratio $NH_3/NO_X$.

Figure 3C:
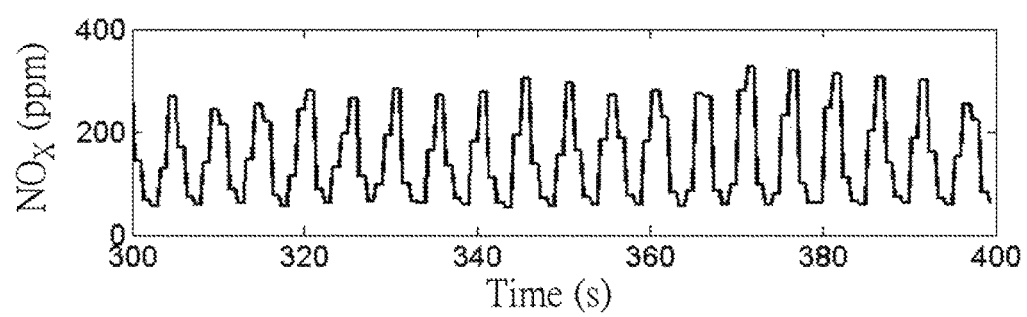
FIG. 3C is an enlarged diagram from 300 sec to 400 sec of FIG. 3A.

In FIG. 3A, the second gas sensing signal is less noisy at the stoichiometric point (the concentration ratio $NH_3/NO_X$ equals 1, around 500 to 600 sec) when the lowest $NO_X$ emission without perceptible ammonia leakage is achieved. More oscillatory sensor signals are observed when less urea is injected (the concentration ratio $NH_3/NO_X$ less than 1, before 400 sec). The cross-sensitivity of the SNS to the ammonia concentration for higher-than-stoichiometric ammonia injection is also observed in FIG. 3A (the ratio of $NH_3$ to $NO_X$ greater than 1, after 700 sec). The SNS signal level cannot be interpreted in a straight-forward way as it is not clear whether $NO_X$ or $NH_3$ is excess. FIG. 3C is an enlarged diagram from 300 sec to 400 sec of FIG. 3A. The SNS signal is still oscillatory and cannot be interpreted in a straight-forward way as it is not clear whether $NO_X$ or $NH_3$ is excess.

FIGS. 4A to 4D illustrate Magnitude—Frequency diagrams of second gas sensing signals at different concentration ratio $NH_3/NO_X$ of the present disclosure. In an effort to identify the cross-sensitivity of the SNS, spectral analysis of the SNS signals is conducted by using Fast Fourier Transform (FFT), and the results are shown in FIG. 4A to FIG. 4D.

Figure 4A:
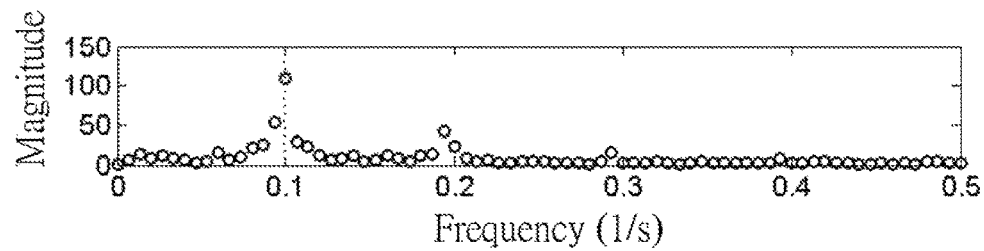
FIGS. 4A to 4D illustrate Magnitude—Frequency diagrams of second gas sensing signals at different concentration ratio $NH_3/NO_X$ of the present disclosure.

In FIG. 4A, the ratio of $NH_3/NO_X$ is about 0.35, the $NH_3$ injection frequency is 0.1 (1/s). It is obvious that the $NO_X$ peak frequency signal and the $NH_3$ injection frequency (dashed line) are both about 0.1 (1/s) it presents that there is no singular between the $NO_X$ peak frequency signal and the $NH_3$ injection frequency, that is, no gas cross-sensitivity effect occur, and the SNS signal reflects the concentration of $NO_X$.

Figure 4B:
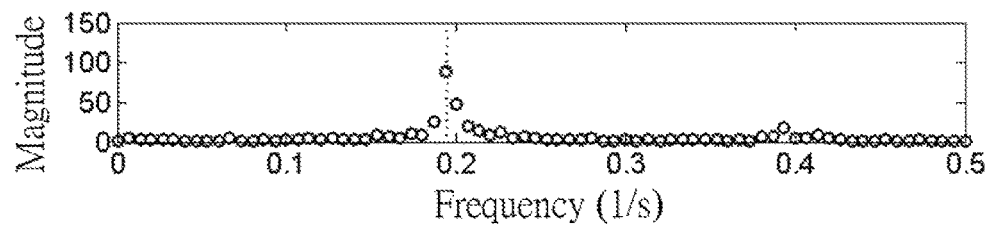

In FIG. 4B, the ratio of $NH_3/NO_X$ is about 0.65, the $NH_3$ injection frequency is 0.195 (1/s). It is obvious that the $NO_X$ peak frequency signal and the $NH_3$ injection frequency (dashed line) are both about 0.2 (1/s). It presents that there is no singular between the $NO_X$ peak frequency signal and the $NH_3$ injection frequency, that is, no gas cross-sensitivity effect occur, and the SNS signal reflects the concentration of $NO_X$.

Figure 4C:
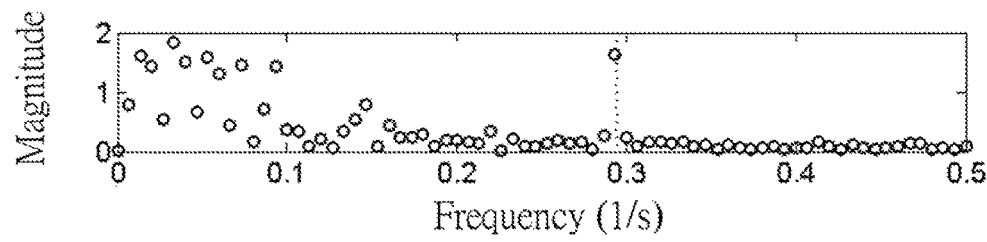

In FIG. 4C, the ratio of $NH_3/NO_X$ is about 1, the $NH_3$ injection frequency is 0.295 (1/s). It is obvious that the $NO_X$ peak frequency signal and the $NH_3$ injection frequency (dashed line) are both about 0.3 (1/s). It presents that there is no singular between the $NO_X$ peak frequency signal and the $NH_3$ injection frequency, that is, no gas cross-sensitivity effect occur, and the SNS signal reflects the concentration of $NO_X$.

Figure 4D:
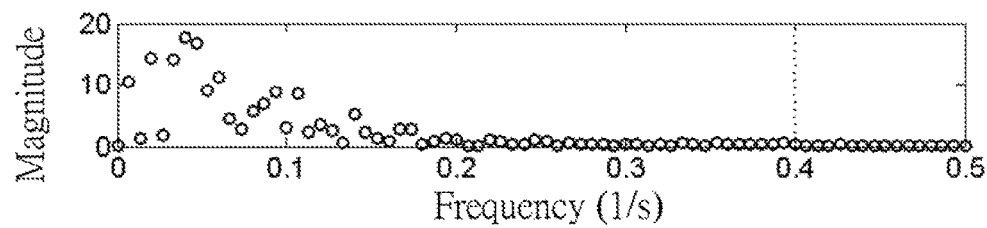

In FIG. 4D, the ratio of $NH_3/NO_X$ is about 1.35, the $NH_3$ injection frequency is 0.4 (1/s). It is obvious that the distance between $NO_X$ peak frequency signal and the $NH_3$ injection frequency (dashed line) is large. It presents that there has singular between the $NO_X$ peak frequency signal and the $NH_3$ injection frequency, that is, gas cross-sensitivity effect occur, and the SNS signal does not reflects the concentration of $NO_X$.

The present disclosure is about gas cross-sensitivity analysis method and system thereof, and is applicable to the detection engine exhaust, engine vehicle exhaust testing and related fields with gas cross-sensitivity effect.

In summary, the foregoing method and system of the present disclosure is to identify the cross-sensitivity of the second sensing unit (SNS) to ammonia, spectral analysis of the second gas sensing signal from a second sensing unit with perturbed urea injection rate is conducted by using Fast Fourier Transform (FFT). The spectral analysis reveals that the amplitude of the SNS signal at the perturbed injection frequency can be used for direct interpretation of the true $NO_X$ emission in applications where ammonia is involved. A comparison between the $NO_X$ peak frequency signal and the $NH_3$ injection frequency tells when the second gas sensing signal represents the true $NO_X$ concentration and when significant $NH_3$ leakage occurs.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the invention. In view of the foregoing, it is intended that the present disclosure cover modifications and variations of this invention provided they fall within the scope of the following claims.

What is claimed is:

1. A gas cross-sensitivity analysis method, comprising:
   generating an injection frequency signal from a first gas;
   capturing a second gas sensing signal from a second gas;
   converting the second gas sensing signal to a second gas sensing frequency signal;
   determining a peak frequency of the second gas sensing frequency signal, and generating a sensing peak frequency signal; and
   generating a subtracted value by subtracting the sensing peak frequency signal from the injection frequency signal, and taking an absolute value of the subtracted value as a difference;
   wherein if the difference is less than a standard value, the second gas sensing signal is indicated to be valid, otherwise if the difference is greater than the standard value, the second gas sensing signal is indicated to be invalid, then a singular is occurred between the injection frequency signal and the sensing peak frequency signal thereby inducing a gas cross-sensitivity effect.

2. The gas cross-sensitivity analysis method of claim 1, wherein the second gas sensing signal is converted to the second gas sensing frequency signal using a Fast Fourier Transform.

3. A gas cross-sensitivity analysis system, comprising:
   a first gas generating unit, wherein the first gas generating unit generates an injection frequency signal from a first gas;
   a second sensing unit, wherein the second sensing unit captures a second gas sensing signal from a second gas;
   a signal converting unit electrically connected to the second sensing unit, wherein the signal converting unit converts the second gas sensing signal to a second gas sensing frequency signal using a Fast Fourier Transform;
   a peak frequency judging unit electrically, connected to the signal converting unit, wherein the peak frequency judging unit determines a peak frequency of the second gas sensing frequency signal and outputting a sensing peak frequency signal; and
   a signal analyzing unit electrically connected to the first gas generating unit and the peak frequency judging unit, wherein the signal analyzing unit analyzes the injection frequency signal and the sensing peak frequency signal to determine whether a cross-sensitivity effect is produced.

4. The gas cross-sensitivity analysis system of claim 3, further comprising:
   a selective catalytic reduction nit connected to the first gas generating unit and a second sensing unit.

5. The gas cross-sensitivity analysis system of claim 4, wherein the selective catalytic reduction unit converts the second gas into a non-toxic gas using the first gas.

6. The gas cross-sensitivity analysis system of claim 5, wherein the first gas is an ammonia, and the second gas is a nitrogen oxide.

7. The gas cross-sensitivity analysis system of claim 3, wherein the injection frequency signal is an ammonia injection frequency signal.

8. The gas cross-sensitivity analysis system of claim 3, wherein the second sensing unit is a nitrogen oxide sensor.

9. The gas cross-sensitivity analysis system of claim 3, wherein the first gas is produced from a vaporization of an urea aqueous solution.

* * * * *